(12) United States Patent
Von Berg et al.

(10) Patent No.: US 8,903,153 B2
(45) Date of Patent: Dec. 2, 2014

(54) BONE SUPPRESSION IN X-RAY RADIOGRAMS

(75) Inventors: Jens Von Berg, Hamburg (DE); Ulrich Neitzel, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 232 days.

(21) Appl. No.: 13/517,259

(22) PCT Filed: Dec. 16, 2010

(86) PCT No.: PCT/IB2010/055876
§ 371 (c)(1),
(2), (4) Date: Jun. 20, 2012

(87) PCT Pub. No.: WO2011/077334
PCT Pub. Date: Jun. 30, 2011

(65) Prior Publication Data
US 2012/0257810 A1    Oct. 11, 2012

(30) Foreign Application Priority Data
Dec. 22, 2009  (EP) .................................... 09180414

(51) Int. Cl.
*G06K 9/00*    (2006.01)
*G06K 9/34*    (2006.01)
*G06K 9/40*    (2006.01)
*G06T 7/00*    (2006.01)

(52) U.S. Cl.
CPC ..... *G06T 7/0083* (2013.01); *G06T 2207/30008* (2013.01); *G06T 2207/10116* (2013.01)
USPC ............................. 382/132; 382/173; 382/275

(58) Field of Classification Search
USPC ................................ 382/132, 173
See application file for complete search history.

(56) References Cited

U.S. PATENT DOCUMENTS 4,792,900 A    12/1988  Sones et al.
5,832,134 A    11/1998  Avinash et al.
(Continued)

FOREIGN PATENT DOCUMENTS

EP    11748386 A1    1/2007

OTHER PUBLICATIONS

Reed et al, "X-Ray Reconstruction of the Spinal Cord, Using Bone Suppression", IEEE Transactions on Biomedical Engineering, vol. BME-27, No. 6, Jun. 1980, pp. 293-298.
(Continued)

*Primary Examiner* — Utpal Shah

(57) ABSTRACT

The invention relates to a system (100) for extracting an object (Ob) from a source image, said object being delineated by a contour (C), the system (100) comprising a gradient unit (110) for computing the source image gradient field, based on the source image, a smoothing unit (120) for smoothing the source image gradient field, and an integration unit (130) for calculating an object image by integrating the smoothed source image gradient field, thereby extracting the object (Ob) from the source image. At each point of the source image, the smoothing is defined by a 2-dimensional convolution kernel which is a product of a first 1-dimensional convolution kernel in the first direction substantially parallel to the contour (C), and a second 1-dimensional convolution kernel in the second direction substantially normal to the contour (C). The first 1-dimensional convolution kernel defines smoothing within each region separated by the contour, while the second 1-dimensional convolution kernel defines smoothing across the contour separating two regions, independently of the orientation of the object and the contour curvature.

20 Claims, 6 Drawing Sheets

(56) References Cited

U.S. PATENT DOCUMENTS

| | | | |
|---|---|---|---|
| 7,545,965 B2* | 6/2009 | Suzuki et al. | 382/128 |
| 8,233,692 B2* | 7/2012 | Merlet | 382/132 |
| 2003/0086596 A1* | 5/2003 | Hipp et al. | 382/128 |
| 2005/0100208 A1 | 5/2005 | Suzuki et al. | |
| 2008/0123998 A1 | 5/2008 | Gomi et al. | |
| 2009/0060366 A1 | 3/2009 | Worrell et al. | |
| 2009/0087070 A1 | 4/2009 | Slabaugh et al. | |
| 2009/0214099 A1 | 8/2009 | Merlet | |

OTHER PUBLICATIONS

Rasheed et al, "Rib Suppression in Frontal Chest Radiographs: A Blind Source Separation Approach", Signal Prpocessing and Its Applications, 2007, pp. 104.

Lell et al, "New Techniques in CT Angiography", Clinical Applications of Vascular Imaging, Ref vol. 26, 2006, pp. S45-S63.

Zhao et al, "Enhanced Lung Cancer Detection in Temporal Subtraction Chest Radiography Using Directional Edge Filtering Techniques", Proceedings of SPIE, vol. 4684, Jan. 1, 2002, pp. 1-6.

Simko et al, "Elimination of Clavicle Shadows to Help Automatic Lung Nodule Detection on Chest Radiographs", IFMBE Proceedings, 2008, vol. 22, pp. 488-491.

Blaffert et al, "Bone Suppression in CT Angiography Data by Region-Based Multi-Resolution Segmentation", Medical Imaging, Proceedings of SPIE, 2003, vol. 5032, pp. 527-534.

Barthel et al, "Robust Automatic Lung Field Segmentation Ondigital Chest Radiographs", In. J. Cars, vol. 4, Supplement 1, 2009, 2 Pages.

* cited by examiner

BONE SUPPRESSION IN X-RAY RADIOGRAMS

FIELD OF THE INVENTION

The invention relates to extracting and suppressing obstructing objects in images.

BACKGROUND OF THE INVENTION

For many diagnostic purposes it is beneficial to remove bone shadows from a radiograph image. In the image with removed bone shadows, some findings can be made easier because bone shadows removed from the image no longer interfere with subtle soft tissue structures. For example, lung nodule detection can be improved by this technique by removing rib shadows. Removing bone shadows can be useful both for a human reader and a lung nodule CAD (Computer Assisted Detection) system, because the risk of missing lung nodules covered by rib shadows (false negatives) or identifying false nodules at rib-shadow crossings (false positives) is reduced.

A known method of obtaining better soft tissue images relies on using dual energy acquisition. However, using dual energy acquisition requires special x-ray equipment and a higher x-ray dose exposure to the patient.

Another approach is disclosed by Simkó et al in "Elimination of clavicle shadows to help automatic lung nodule detection on chest radiographs", published in Vander Sloten et al. (Eds.) IFMBE Proceedings 22, 488-491, 2008. Here a clavicle contour is segmented and described by a parametric curve $\{x(s), y(s)\}_{s \in [0, 1]}$. A neighborhood of the clavicle contour is defined as a set of the points $(x(s), y(s)+d)$, wherein $s \in [0, 1]$ and $d \in [\delta, +\delta]$ for some positive number $\delta$. A clavicle image is reconstructed by
1. Calculating the gradient image.
2. Building a bone model.
3. Recalculating the image from a modified gradient image The bone model is built by smoothing in the $\{(s, d)|s \in [0, 1]$ and $d \in [\delta, +\delta]\}$ space, using 1-dimensional Gaussian kernels with a large standard distribution $\sigma_s$ in the direction of the s variable, tangential with respect to the contour, and a small standard distribution $\sigma_d$ in the direction of the y axis. The clavicle image is subtracted from the original image, yielding a soft tissue image with suppressed clavicle. A shortcoming of the above method is that it is assumed that the bone lies in a horizontal direction.

US 2009/0214099 discloses using a global affine transformation to reorient objects in an image. The bone shadows in the transformed image are then suppressed. For example, the method described by Simkó et al may be applied to suppress the clavicle oriented perpendicularly to the y axis. The image with suppressed clavicle is then transformed by the inverse of the global affine transformation to reorient objects in an image to their original positions. However, the method will not perform well when the contour of the bone is curved, which is substantially the case for every closed contour, for example.

SUMMARY OF THE INVENTION

It would be advantageous to have a system for suppressing obstructing objects in an image, which performs well for curved objects.

To achieve this, in an aspect, the invention provides a system for extracting an object from a source image, said object being delineated by a contour, the system comprising a gradient unit for computing the source image gradient field, based on the source image, a smoothing unit for smoothing the source image gradient field, and an integration unit for calculating an object image by integrating the smoothed source image gradient field, thereby extracting the object from the source image, characterized in that at each point of the source image, the smoothing is defined by a 2-dimensional convolution kernel which is a product of a first 1-dimensional convolution kernel in the first direction substantially parallel to the contour, and of a second 1-dimensional convolution kernel in the second direction substantially normal to the contour. The first 1-dimensional convolution kernel defines smoothing along the contour, in regions on both sides of the contour, while the second 1-dimensional convolution kernel defines smoothing across the contour separating the two regions, independently of the orientation of the object and of the contour curvature.

In an embodiment, the system further comprises a coordinate unit for:

parameterizing the contour, and transforming Cartesian coordinates (x, y) in the source image into contour-based coordinates (s, n), wherein s(x, y) is the value of the parameter of the point on the parameterized contour, corresponding to the intersection of the normal to the contour extending through the point (x, y), wherein n(x, y) is a signed distance between the point (x, y) in the source image and the contour, and wherein the signed distance assumes one sign for points on one side of the contour and the opposite sign for points on the other side of the contour, and wherein the first 1-dimensional convolution kernel is dependent on the s coordinate and the second 1-dimensional convolution kernel is dependent on the n coordinate. Implementing the 1-dimensional convolution kernels of the smoothing operator is thus made easier.

In an embodiment, the system further comprises a subtraction unit for subtracting the object image from the source image, thereby creating a suppression image wherein the object is suppressed.

In an embodiment of the system, the standard deviation of the first 1-dimensional convolution kernel is at least one order of magnitude greater than the standard deviation of the second 1-dimensional convolution kernel. Assuming that the contribution of the object to the source image intensities (i.e. pixel values) is similar at neighboring locations on the object outlined by the contour in the source image, which is typically the case for bone shadows, the integrated smoothed gradient will yield the object image, when the smoothing is performed primarily in a direction parallel to the object contour. This can be achieved by using smoothing kernels with a standard deviation of the first 1-dimensional convolution kernel that is much greater than a standard deviation of the second 1-dimensional convolution kernel.

In an embodiment of the system, the standard deviation of the first 1-dimensional convolution kernel has the length of at least 1% of the contour length. Because smoothing defined by the first kernel averages gradient field vectors within the regions defined by the contour, but not across the contour, a large standard deviation (i.e. having the length of at least 1%, preferably of at least 5% of the contour length) smoothes source image gradient fields within said regions without affecting the edges along the contour. The comparison of the source image gradient field and the smoothed source image gradient field allows extracting information on subtle details of the source image, which details are hidden by the object In an embodiment of the system, the smoothing unit is further adapted for correcting the source image gradient vector orientation at each point, based on the orientation of the contour normal extending through the point with respect to the orientation of the contour normal extending through an origin of the 2-dimensional convolution kernel. This approach averages the source image gradient vectors relative to the contour normal along the contour.

In an embodiment of the system, the smoothing unit is further adapted for compensating the smoothed source image gradient field in order to assure that the sum of smoothed source image gradient field vectors along a line across a region of interest comprised in the source image is substantially similar to the corresponding sum of the source image gradient field vectors. Thus, after subtracting the object image from the source image, the object should substantially disappear in the suppression image, but the region outside the object contour should be substantially unchanged in the suppression image.

In an embodiment of the system, the contour is closed. This embodiment of the system is used for suppressing objects which are enclosed in the image in their entirety.

In a further aspect, the system according to the invention is used for extracting bone shadows in x-ray images.

In a further aspect, the system according to the invention is comprised in an image acquisition apparatus.

In a further aspect, the system according to the invention is comprised in a workstation.

In a further aspect, the invention provides a method of extracting an object from a source image, said object being delineated by a contour, the method comprising:
  a gradient step for computing the source image gradient field, based on the source image,
  a smoothing step for smoothing the source image gradient field, and
  an integration step for calculating an object image by integrating the smoothed source image gradient field, thereby extracting the object from the source image, characterized in that at each point of the source image the smoothing is defined by a 2-dimensional convolution kernel which is a product of a first 1-dimensional convolution kernel in the first direction substantially parallel to the contour, and of a second 1-dimensional convolution kernel in the second direction which is substantially normal to the contour.

In a further aspect, the invention provides a computer program product to be loaded by a computer arrangement, comprising instructions for extracting an object from a source image, said object being delineated by a contour, the computer arrangement comprising a processing unit and a memory, the computer program product, after being loaded, providing said processing unit with the capability to carry out steps of the method according to the invention.

It will be appreciated by those skilled in the art that two or more of the above-mentioned embodiments, implementations, and/or aspects of the invention may be combined in any way deemed useful.

Modifications and variations of the system, of the image acquisition apparatus, of the workstation, of the method, and/or of the computer program product, which correspond to the described modifications and variations of the system or of the method, can be carried out by a person skilled in the art on the basis of the description.

A person skilled in the art will appreciate that the multidimensional image in the claimed invention may be 2-dimensional (2-D) image data, acquired by various acquisition modalities such as, but not limited to, X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). A person skilled in the art will further be able to modify the system and/or method of the invention to make it suitable for 3-dimensional (3-D) image data.

The invention is defined in the independent claims. Advantageous embodiments are defined in the dependent claims.

BRIEF DESCRIPTION OF THE DRAWINGS

These and other aspects of the invention will be apparent from and elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1:
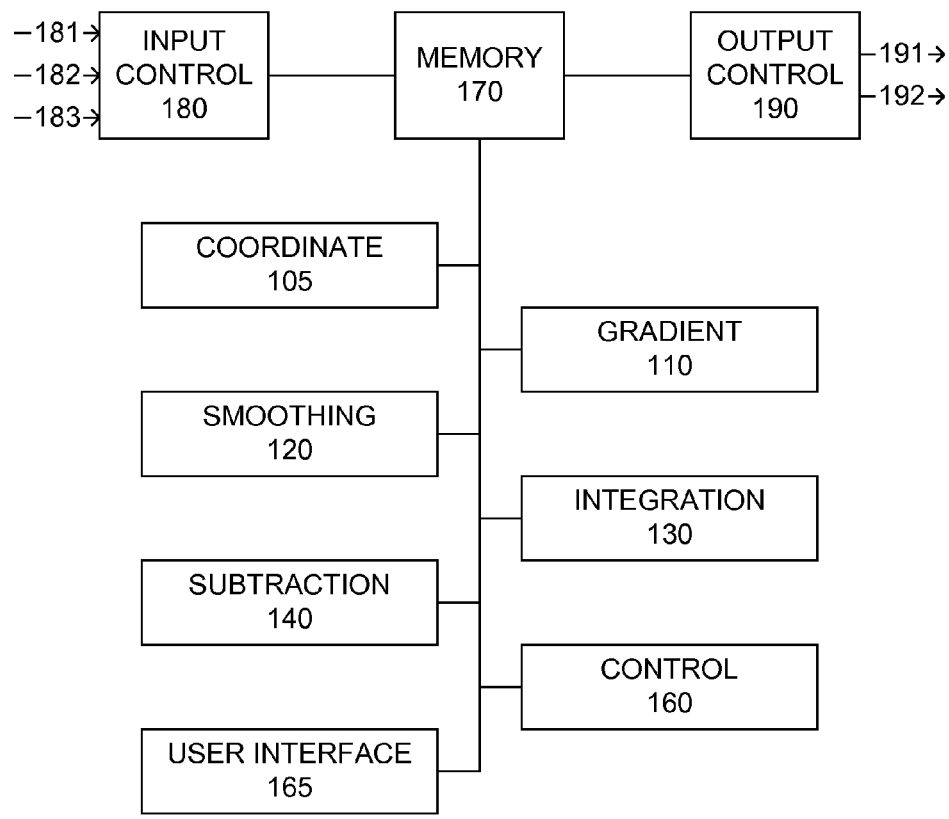
FIG. 1 shows a block diagram of an exemplary embodiment of the system.

FIG. 1 schematically shows a block diagram of an exemplary embodiment of the system 100 for extracting an object from a source image, said object being delineated by a contour system 100 comprising
  a gradient unit 110 for computing the source image gradient field, based on the source image,
  a smoothing unit 120 for smoothing the source image gradient field, and
  an integration unit 130 for calculating an object image by integrating the smoothed source image gradient field, thereby extracting the object from the source image, characterized in that at each point of the source image, the smoothing is defined by a 2-dimensional convolution kernel which is a product of a first 1-dimensional convolution kernel in the first direction substantially parallel to the contour, and of a second 1-dimensional convolution kernel in the second direction substantially normal to the contour.

The exemplary embodiment of the system 100 further comprises
  a coordinate unit 105 for parameterizing the contour, and for transforming Cartesian coordinates in the source image into contour-based coordinates,
  a subtraction unit 140 for subtracting the object image from the source image, thereby creating a suppression image,
  a control unit 160 for controlling the work of the system 100,
  a user interface 165 for communication between the user and the system 100, and
  a memory unit 170 for storing data.

In an embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

A person skilled in the art will understand that there are many ways to connect input devices to the input connectors 181, 182 and 183 and output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 100, the system 100 comprises a memory unit 170. The system 100 is arranged to receive input data from external devices via any of the input connectors 181, 182, and 183 and store the received input data in the memory unit 170. Loading the input data into the memory unit 170 allows quick access to relevant data portions by the units of the system 100. The input data comprises the source image. Optionally, it may comprise the contour data and user inputs such as the standard deviations of the first and second convolution kernels, for example. The memory unit 170 may be implemented by devices such as, but not limited to, a register file of a CPU, a cache memory, a Random Access Memory (RAM) chip, a Read Only Memory (ROM) chip, and/or a hard disk drive and a hard disk. The memory unit 170 may be further arranged to store the output data. The output data comprises the object image and/or the suppression image. The memory unit 170 may be also arranged to receive data from and/or deliver data to the units of the system 100 comprising the coordinate unit 105, the gradient unit 110, the smoothing unit 120, the integration unit 130, the subtraction unit 140, the control unit 160, and the user interface 165, via a memory bus 175. The memory unit 170 is further arranged to make the output data available to external devices via any of the output connectors 191 and 192. Storing data from the units of the system 100 in the memory unit 170 may advantageously improve the performance of the units of the system 100 as well as the rate of transfer of the output data from the units of the system 100 to external devices.

In an embodiment of the system 100, the system 100 comprises a control unit 160 for controlling the system 100. The control unit 160 may be arranged to receive control data from and provide control data to the units of the system 100. For example, after computing the source image gradient field, the gradient unit 110 may be arranged to provide control data "the gradient field is computed" to the control unit 160, and the control unit 160 may be arranged to provide control data "smooth the gradient field" to the smoothing unit 120. Alternatively, a control function may be implemented in another unit of the system 100.

In an embodiment of the system 100, the system 100 comprises a user interface 165 for communication between a user and the system 100. The user interface 165 may be arranged to receive a user input comprising two standard deviations for the first and second convolution kernels. Optionally, the user interface may receive a user input for selecting a mode of operation of the system such as, e.g. for using a particular convolution kernel function such as a Gaussian or nearest neighbor smoother kernel function. The user interface is further arranged to display the object image and/or the suppression image. A person skilled in the art will understand that more functions may be advantageously implemented in the user interface 165 of the system 100.

In the embodiments described below, the source image is a medical image of the chest and the object comprises the bones potentially obscuring the view of nodules in the lungs: the ribs and the clavicle. A person skilled in the art will understand that these embodiments illustrate the invention and must not be construed as limiting the scope of the claims.

In an embodiment, the input to the system comprises a contour of the bones, ribs and clavicle. Alternatively, the system 100 may comprise a contour unit for delineating ribs and clavicle in the source image, using segmentation of the source image or of the source image gradient field. The system 100 comprises a coordinate unit 105 for:
  parameterizing the contour, and
  transforming Cartesian coordinates (x, y) in the source image into contour-based coordinates (s, n), wherein s(x, y) is the value of the parameter of the point on the parameterized contour, corresponding to the intersection of the normal to the contour extending through the point (x, y), wherein n(x, y) is a signed distance between the point (x, y) in the source image and the contour, and wherein the signed distance assumes one sign for points on one side of the contour and the opposite sign for points on the other side of the contour.

Figure 2A:
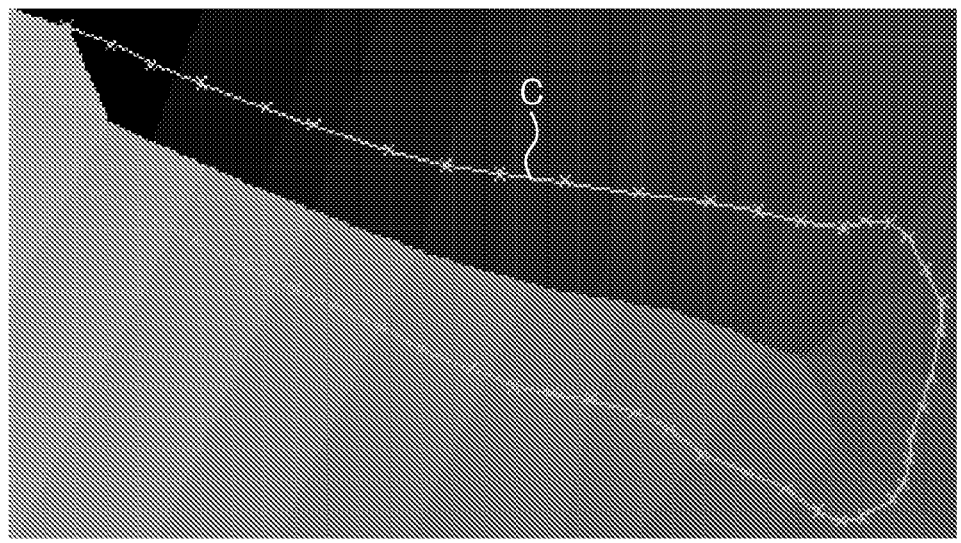
FIG. 2A illustrates the s(x, y) coordinates of the coordinate transform (x, y)→(s, n)
Figure 2B:
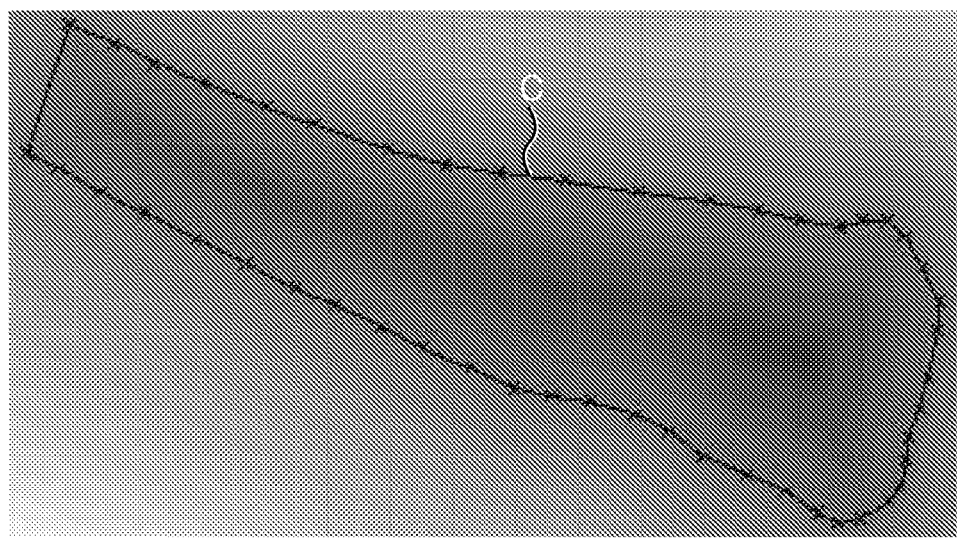
FIG. 2B illustrates the n(x, y) coordinates of the coordinate transform (x, y)→(s, n)

FIG. 2A illustrates the s(x, y) coordinates of the coordinate transform (x, y)→(s, n) and FIG. 2B illustrates the n(x, y) coordinates of the coordinate transform (x, y)→(s, n). The parameter s is a cyclic distance along the contour, measured with respect to an arbitrary reference point on the contour. The signed distance coordinate n is positive outside the contour and negative inside the contour. The shown contour C is closed and delineates a portion of the clavicle contour. The contour C, approximated by a discrete stepwise linear approximation, is obtained using segmentation of the source image as described in Barthel and von Berg, Robust automatic lung field segmentation on digital chest radiographs, Int. J. CARS vol. 4, supplement 1, p. 326, 2009. A level set implementation of bones segmentation is also possible and has the advantage that it already uses a parametric representation of the contour. The level set framework further provides a distance function for use as the n variable.

The transformed coordinate (s, n) of a given image position (x, y) is obtained by a table providing (s, n) values for each (x, y) position. This table was built by a discrete sampling of s and n parameters along the contour. A table entry for (x, y) is replaced whenever a novel candidate has a lower absolute n value, which means it is closer to the contour. The (s, n) coordinates are well suited for defining the first and second convolution kernel.

Figure 3A:
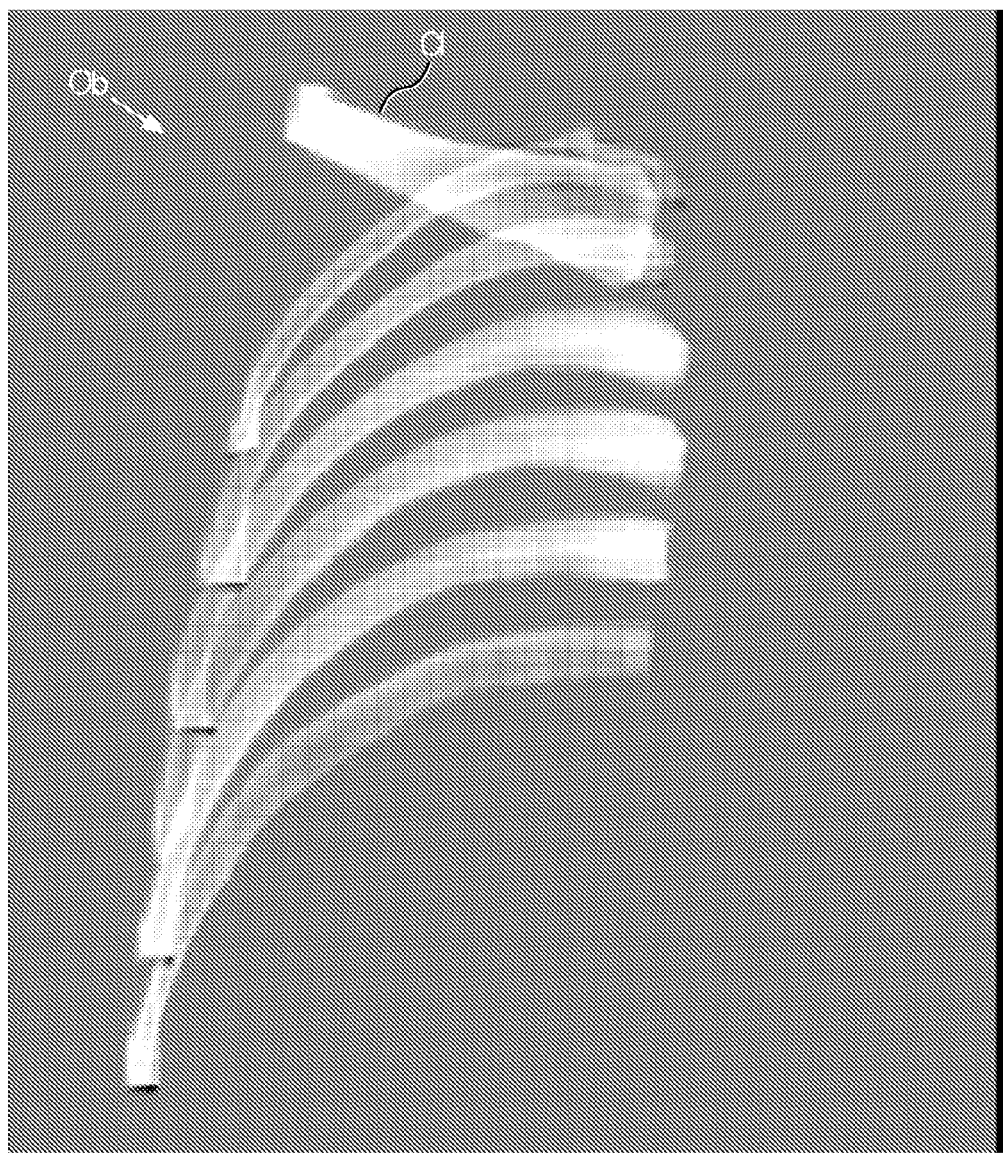
FIG. 3A shows an exemplary object image.

FIG. 3A shows an exemplary object image—the image of the object Ob comprising bone components of the source image, i.e. posterior ribs and clavicle Cl. This object image was computed by smoothing the source image gradient field with Gaussian kernels. Gaussian kernels are known to a person skilled in the art. The first Gaussian kernel is dependent on the s coordinate and the second Gaussian kernel is dependent on the n coordinate. The standard deviation of the first convolution kernel is $\sigma_s = 40$ mm and the standard deviation of the second convolution kernel is $\sigma_n = 0.2$ mm. In an embodiment, the smoothing unit 120 is adapted for correcting the source image gradient vector orientation before smoothing. The gradient field vector orientation is corrected at each point (s, n), based on the orientation of the contour normal n extending through the point (s, n) with respect to the orientation of the contour normal $n_k$ extending through an origin $(s_k, n_k)$ of the 2-dimensional convolution kernel. The corrected source image gradient field vector orientation can be computed from $\phi(s, n) + \phi(n) - \phi(n_k)$, where $\phi(s, n)$ is the angular coordinate of the gradient field vector at (s, n) and $\phi(n)$ and $\phi(n_k)$ denote the angular coordinates of the normal vectors n and $n_k$, respectively. The gradient absolute value is preserved. This approach averages the source image gradient field along lines perpendicular to the contour normal and parallel to the contour, while preserving the sharp bone edges along the contour. The bone image is reconstructed from the modified gradient image by summation, i.e. by integration of the smoothed source image gradient field, which integration is carried out by the integration unit 130.

In order to speed up the smoothing, i.e. the computing of the convolution of the first convolution kernel and the gradient field, a subset of image positions on the integration curve, e.g. positions generated randomly to uniformly cover the integration curve, can be used.

In order to obtain good bone images, the standard deviation $\sigma_s$ needs to be large with respect to the smoothed object dimension. A possible measure of an object such as a bone is the contour length. Good results are expected with the standard deviation $\sigma_s$ of the order of magnitude of at least 5% of the contour length. However, the application of such a large standard deviation requires that the gradient field varies slowly as a function of the s variable.

In an embodiment of the system, the smoothing unit 120 is further adapted for compensating the smoothed source image gradient field in order to assure that the sum of smoothed source image gradient field vectors along a line across a region of interest comprised in the source image is substantially similar to the corresponding sum of the source image gradient field vectors. This is preferable because the anisotropic smoothing in the (s, n) coordinates modifies gradients in a way that the sum of the smoothed gradient field vectors within the region of interest (the bone with a margin) is modified with respect to the gradient field defined by the source image. During the integration of such a smoothed gradient field, a modified intensity value at the border of the region of interest is obtained, which induces artificial contrast in the reconstructed image. Thus, compensation is preferred in order to assure that the smoothed gradient field vector sum line-total and row-total across the region of interest around the bone is substantially the same as the corresponding vector sum line-total and row-total of the source image gradient field, across the region of interest around the bone.

Figure 3B:
FIG. 3B shows an exemplary suppression image.

FIG. 3B shows an exemplary suppression image—a chest radiograph with bone suppression on the right-hand side of the patient (left-hand side of the image). The right-hand side clavicle and the posterior ribs appear strongly suppressed. However, the left-hand side clavicle and the posterior ribs appear unaffected. The suppression image shown in FIG. 3B is obtained by subtracting the object image shown in FIG. 3A from the source image (not shown), which subtraction is carried out by the subtraction unit 140 of the system 100. With the bone shadow Ob subtracted from the source image, the suppression image shows soft tissue structures of the left lung.

A person skilled in the art will appreciate that the system 100 may be a valuable tool for assisting a physician in many aspects of her/his job. Further, although the embodiments of the system are illustrated using medical applications of the system, non-medical applications of the system are also contemplated.

Those skilled in the art will further understand that other embodiments of the system 100 are also possible. It is possible, among other things, to redefine the units of the system and to redistribute their functions. Although the described embodiments apply to medical images, other applications of the system, not related to medical applications, are also possible.

The units of the system 100 may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 4:
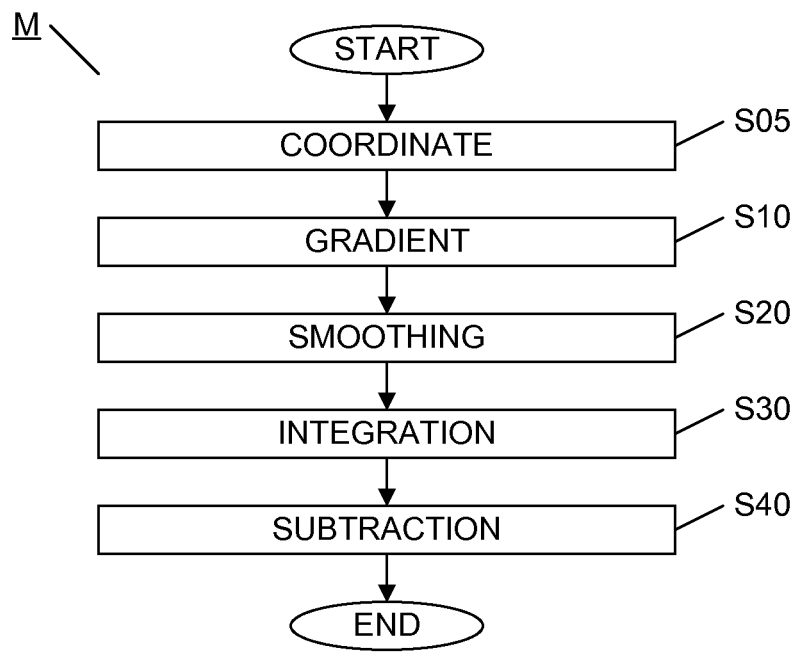
FIG. 4 shows a flowchart of an exemplary implementation of the method.

A flowchart of an exemplary implementation of the method M of extracting an object Ob from a source image, said object being delineated by a contour C, is shown in FIG. 4. The method M begins with a coordinate step S05 for parameterizing the contour, and for transforming Cartesian coordinates (x, y) in the source image into contour-based coordinates (s, n). After the coordinate step S05, the method M continues to a gradient step S10 for computing the source image gradient field, based on the source image. After the gradient step S10, the method M continues to a smoothing step S20 for smoothing the source image gradient field. After the smoothing step S20, the method M continues to an integration step S30 for integrating the smoothed source image gradient field, thereby extracting the object from the source image. After the integration step S30, the method M continues to a subtraction step S40 for subtracting the object image from the source image, thereby creating a suppression image. After the subtraction step S40, the method terminates.

The smoothing step S20 of the method M is characterized in that at each point of the source image, the smoothing is defined by a 2-dimensional convolution kernel which is a product of a first 1-dimensional convolution kernel in the first direction substantially parallel to the contour, and of a second 1-dimensional convolution kernel in the second direction substantially normal to the contour.

A person skilled in the art may change the order of some steps, add some optional steps (e.g. segmentation) or omit some non-mandatory steps (e.g. correcting gradient field vector orientations), or perform some steps concurrently using threading models, multi-processor systems or multiple processes without departing from the concept as intended by the present invention. Optionally, two or more steps of the method M may be combined into one step. Optionally, a step of the method M may be split into a plurality of steps.

Figure 5:
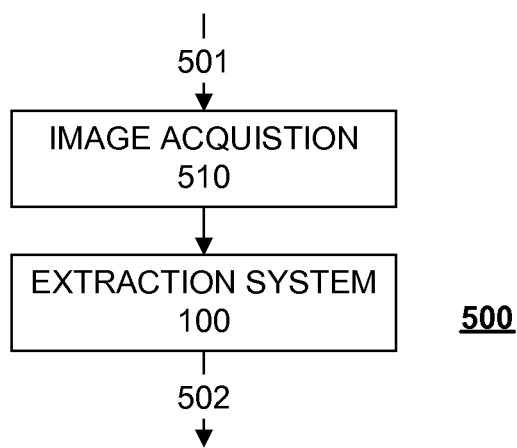
FIG. 5 schematically shows an exemplary embodiment of the image acquisition apparatus.

FIG. 5 schematically shows an exemplary embodiment of the image acquisition apparatus 500 employing the system 100 of the invention, said image acquisition apparatus 500 comprising an image acquisition unit 510 connected via an internal connection with the system 100, an input connector 501, and an output connector 502. This arrangement advantageously increases the capabilities of the image acquisition apparatus 500, providing said image acquisition apparatus 500 with advantageous capabilities of the system 100.

Figure 6:
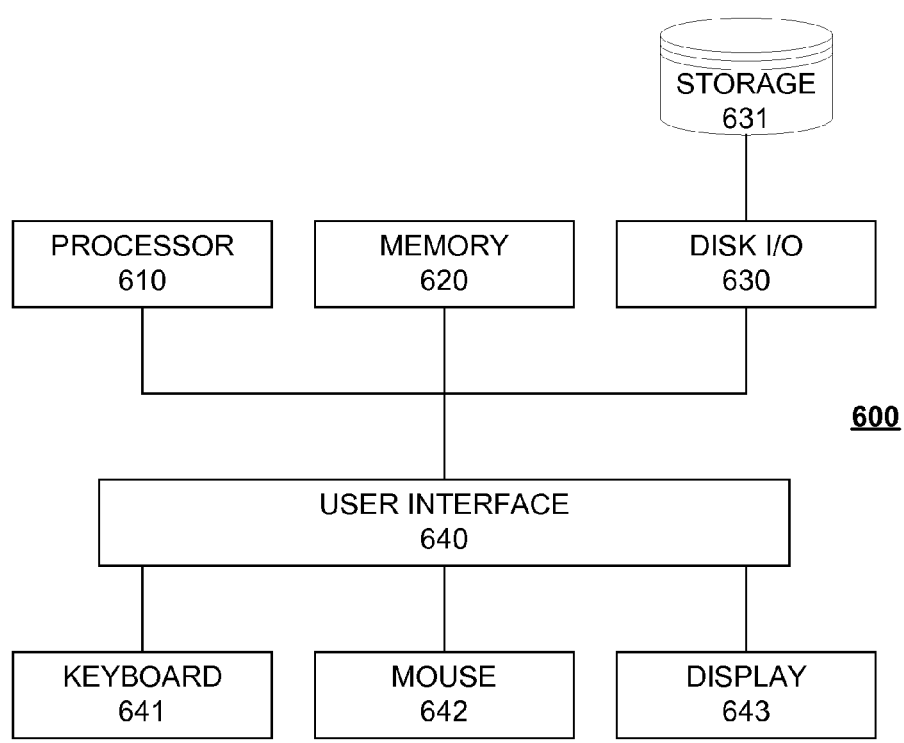
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. A person skilled in the art will understand that there are numerous other embodiments of the workstation 600 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same record of hardware or software. The usage of the words first, second, third, etc., does not indicate any ordering. These words are to be interpreted as names.

The invention claimed is:

1. A system for extracting an object from a source image, said object being delineated by a contour, the system comprising:
    a gradient unit that computes the source image gradient field, based on the source image,
    a smoothing unit that smoothes the source image gradient field,
    a coordinate unit that:
        parameterizes the contour, and
        transforms Cartesian coordinates of a point (x, y) in the source image into contour-based coordinates (s, n), wherein s(x, y) is a value of a parameter of the point (x, y) on the parameterized contour corresponding to an intersection of a normal to the contour extending through the point (x, y), wherein n(x, y) is a signed distance between the point (x, y) in the source image and the contour, and wherein the signed distance assumes one sign for points on one side of the contour and an opposite sign for points on the other side of the contour and wherein a first 1-dimensional convolution kernel is dependent on the s coordinate and a second 1-dimensional convolution kernel is dependent on the n coordinate, and
    an integration unit that calculates an object image by integrating the smoothed source image gradient field, thereby extracting the object from the source image,
    wherein at each point of the source image, the smoothing is defined by a 2-dimensional convolution kernel which is a product of the first 1-dimensional convolution kernel in a first direction substantially parallel to the contour, and of the second 1-dimensional convolution kernel in a second direction substantially normal to the contour.

2. A system as claimed in claim 1, further comprising a subtraction unit that subtracts the object image from the source image, thereby creating a suppression image, wherein the object is suppressed.

3. A system as claimed in claim 1, wherein a standard deviation of the first 1-dimensional convolution kernel is at least one order of magnitude greater than a standard deviation of the second 1-dimensional convolution kernel.

4. A system as claimed in claim 1, wherein a standard deviation of the first 1-dimensional convolution kernel has a length of at least 1% of a length of the contour.

5. A system as claimed in claim 1, wherein the smoothing unit corrects a source image gradient vector orientation at each point, based on the orientation of the contour normal extending through the point with respect to the orientation of the contour normal extending through an origin of the 2-dimensional convolution kernel.

6. A system as claimed in claim 1, wherein the smoothing unit compensates the smoothed source image gradient field in order to assure that a sum of smoothed source image gradient field vectors along a line across a region of interest comprised in the source image is substantially similar to a corresponding sum of the source image gradient field vectors.

7. A system as claimed in claim 1, wherein the contour is closed.

8. An image acquisition apparatus comprising a system as claimed in claim 1.

9. A workstation comprising a system as claimed claim 1.

10. A method of extracting an object from a source image, said object being delineated by a contour, the method comprising:
    computing the source image gradient field, based on the source image,
    smoothing the source image gradient field,
    parameterizing the contour,
    transforming Cartesian coordinates of a point (x, y) in the source image into contour-based coordinates (s, n), wherein s(x, y) is a value of a parameter of the point (x, y) on the parameterized contour corresponding to an intersection of a normal to the contour extending through the point (x, y), wherein n(x, y) is a signed distance between the point (x, y) in the source image and the contour, and wherein the signed distance assumes one sign for points on one side of the contour and an opposite sign for points on the other side of the contour, and wherein a first 1-dimensional convolution kernel is dependent on the s coordinate and a second 1-dimensional convolution kernel is dependent on the n coordinate, and
    calculating an object image by integrating the smoothed source image gradient field, thereby extracting the object from the source image,
    wherein at each point of the source image the smoothing is defined by a 2-dimensional convolution kernel which is a product of the first 1-dimensional convolution kernel in a first direction substantially parallel to the contour, and of the second 1-dimensional convolution kernel in a second direction substantially normal to the contour.

11. A method as claimed in claim 10, wherein a standard deviation of the first 1-dimensional convolution kernel is at least one order of magnitude greater than a standard deviation of the second 1-dimensional convolution kernel.

12. A method as claimed in claim 10, wherein a standard deviation of the first 1-dimensional convolution kernel has a length of at least 1% of a length of the contour.

13. The method as claimed in claim 10, including subtracting the object image from the source image, thereby creating a suppression image, wherein the object is suppressed.

14. A non-transitory computer-readable medium that includes a program that, when executed by a processor, causes the processor to extract an object from a source image by:
computing a source image gradient field, based on the source image,
smoothing the source image gradient field,
parameterizing a contour that delineates the object,
transforming Cartesian coordinates of a point (x, y) in the source image into contour-based coordinates (s, n), wherein s(x, y) is a value of a parameter of the point (x, y) on the parameterized contour corresponding to an intersection of a normal to the contour extending through the point (x, y), wherein n(x, y) is a signed distance between the point (x, y) in the source image and the contour, and wherein the signed distance assumes one sign for points on one side of the contour and an opposite sign for points on the other side of the contour, and wherein a first 1-dimensional convolution kernel is dependent on the s coordinate and a second 1-dimensional convolution kernel is dependent on the n coordinate, and
calculating an object image by integrating the smoothed source image gradient field, thereby extracting the object from the source image,
wherein at each point of the source image the smoothing is defined by a 2-dimensional convolution kernel which is a product of the first 1-dimensional convolution kernel in a first direction substantially parallel to the contour, and of the second 1-dimensional convolution kernel in a second direction substantially normal to the contour.

15. The medium of claim 14, wherein a standard deviation of the first 1-dimensional convolution kernel is at least one order of magnitude greater than a standard deviation of the second 1-dimensional convolution kernel.

16. The medium of claim 14, wherein a standard deviation of the first 1-dimensional convolution kernel has a length of at least 1% of a length of the contour.

17. The medium of claim 14, wherein the program causes the processor to subtract the object image from the source image, thereby creating a suppression image, wherein the object is suppressed.

18. The medium of claim 14, wherein the program causes the processor to correct a source image gradient vector orientation at each point, based on the orientation of the contour normal extending through the point with respect to the orientation of the contour normal extending through an origin of the 2-dimensional convolution kernel.

19. The medium of claim 14, wherein the program causes the processor to compensate the smoothed source image gradient field in order to assure that a sum of smoothed source image gradient field vectors along a line across a region of interest comprised in the source image is substantially similar to a corresponding sum of the source image gradient field vectors.

20. The medium of claim 14, wherein the contour is closed.

* * * * *